United States Patent
Gabriel et al.

(10) Patent No.: US 7,517,901 B2
(45) Date of Patent: Apr. 14, 2009

(54) P38 MAP KINASE INHIBITORS AND METHODS FOR USING THE SAME

(75) Inventors: Tobias Gabriel, San Francisco, CA (US); Michael Soth, Milpitas, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 104 days.

(21) Appl. No.: 11/509,501

(22) Filed: Aug. 23, 2006

(65) Prior Publication Data

US 2007/0049633 A1  Mar. 1, 2007

Related U.S. Application Data

(60) Provisional application No. 60/712,021, filed on Aug. 25, 2005.

(51) Int. Cl.
*A61K 31/416* (2006.01)
*C07D 231/56* (2006.01)

(52) U.S. Cl. .................... 514/405; 514/709; 548/362.1; 564/84

(58) Field of Classification Search ................. 514/406, 514/608; 548/361.1, 362.5; 564/80
See application file for complete search history.

(56) References Cited

U.S. PATENT DOCUMENTS 2,478,048 A * 8/1949 Kwartler .................. 548/361.1
6,858,638 B2 * 2/2005 Damour et al. ............. 514/405

FOREIGN PATENT DOCUMENTS

WO  WO 2004/014907  2/2004
WO  WO 2005/085249  9/2005

OTHER PUBLICATIONS p38 MAP kinase, Wikipedia encyclopedia.*

* cited by examiner

*Primary Examiner*—Yong Chu
(74) *Attorney, Agent, or Firm*—Robert C. Hall

(57) ABSTRACT

Compounds of formula Ia or Ib:

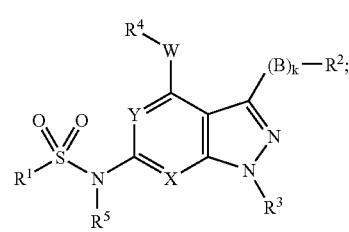

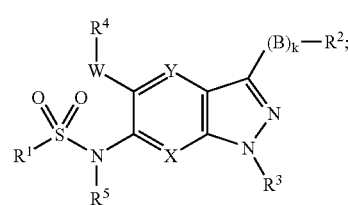

wherein X and Y are nitrogen or $CR^e$, and $R^1$, $R^2$, $R^3$, $R^4$ and $R^5$ are as defined herein. Also disclosed are methods of making the subject compounds and methods of using the compounds for treatment of p38-mediated diseases.

6 Claims, No Drawings

P38 MAP KINASE INHIBITORS AND METHODS FOR USING THE SAME

CROSS-REFERENCE TO RELATED APPLICATIONS

This application is entitled to the benefit of provisional patent application Ser. No. 60/712,021 filed on Aug. 25, 2005, the disclosure of which is incorporated herein by reference.

FIELD OF THE INVENTION

The present invention relates to indazoles, derivatives thereof, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The role of p38 MAP kinase as a therapeutic target in oncology has been reviewed: Podar, K. H.; Teru; Chauhan, Dharminder; Anderson, Kenneth C., "Targeting signalling pathways for the treatment of multiple myeloma", *Expert Opinion on therapeutic Targets* 2005, 9, 359-381; Schultz, R. M., "Potential of p38 MAP kinase inhibitors in the treatment of cancer", *Progress in Drug Research* 2003, 60, 59-92.

The inhibition of these cytokines by inhibition of the p38 kinase is of benefit in controlling, reducing and alleviating many of these disease states.

SUMMARY

The invention provides compounds of formula Ia or Ib:

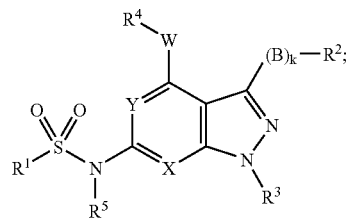

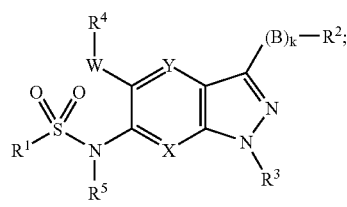

or a pharmaceutically acceptable salt thereof, wherein:

$R^1$ is aryl, heteroaryl, aralkyl or cycloalkyl;

$R^2$ is aryl, heteroaryl, cycloalkyl, branched alkyl or heterocyclyl;

$R^3$ is hydrogen or alkyl;

$R^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, $-(CHR^a)_r-C(=O)-R^b$, $-(CHR^a)_r-O-C(=O)-R^b$, $-(CHR^a)_r-NH-C(=O)-R^b$ or $-SO_2-R^b$, wherein $R^a$ is hydrogen, alkyl or heteroalkyl, $R^b$ is alkyl, hydroxy, amino, heteroalkyl, aryl, aralkyl, heteroaryl, or heterocyclyl, and r is from 0 to 4;

$R^5$ is hydrogen or alkyl;

W is a bond, O, $S(O)_m$, $CH_2$ or $NR^c$, wherein m is from 0 to 2, and $R^c$ is hydrogen, alkyl, heteroalkyl, heterocyclyl, hydroxycycloalkyl, $-C(=O)-R^d$ or $-SO_2-R^d$, wherein $R^d$ is alkyl, aryl, aralkyl, heteroaryl, heteroalkyl or heterocyclyl;

or $R^4$ and $R^c$ together with the atoms to which they are attached may form a heterocyclic ring;

X and Y each independently is nitrogen or $CR^e$, wherein $R^e$ is hydrogen, alkyl, hydroxy, alkoxy, amino, haloalkyl, cyano, halo, heteroalkyl, $C(=O)-R^f$ or $-SO_2-R^f$, wherein $R^f$ is hydrogen, hydroxy or alkyl;

k is 0 or 1; and

B is O, $S(O)_j$, $CH(OR^g)$, $NR^h$, $C(=O)$, or $NR^iC(=O)$, wherein j is 0, 1 or 2;

$R^g$ is hydrogen or alkyl, $R^h$ is hydrogen, alkyl, —C(=O)—$R^j$, or —SO$_2$$R^k$, wherein $R^j$ is alkyl, aryl or aralkyl; and $R^k$ is alkyl, and $R^i$ is alkyl, cycloalkyl, aryl or heteroaryl.

Another aspect of the invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective for p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like. "Branched alkyl" means an alkyl having or more secondary or tertiary carbons, such as isopropyl, isobutyl, tert-butyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonylalkyl" means a moiety of the formula $R^a$—SO$_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkylsulfonyl" means a moiety of the formula —SO$_2$R wherein R is alkyl as defined herein.

"Alkoxycarbonyl" means a group —C(=O)—OR wherein R is alkyl as defined herein.

"Alkoxycarbonylamino" means a group —NR'C(=O)—OR wherein R' is hydrogen or alkyl and R is alkyl as defined herein.

"Alkylcarbonyl" means a group —C(=O)—R wherein R is alkyl as defined herein.

"Aminoalkoxy" means a group —OR—R' wherein R' is amino and R is alkylene as defined herein. "Alkylsulfonylamido" means a moiety of the formula —NR'SO$_2$—R wherein R is alkyl and R' is hydrogen or alkyl.

"Amino" means a radical —NR'R, where R' and R each independently is hydrogen or alkyl.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula $Ar^a$—$R^z$—, where $Ar^a$ is optionally substituted aryl and $R^z$ is alkylene as defined herein.

"Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula $R^c$—$R^d$—, where $R^c$ is cycloalkyl and $R^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl moiety as defined herein wherein one or more, preferably one, two or three, hydrogen atoms have been replaced with a substituent independently selected from the group consisting of —OR$^a$, —NR$^b$R$^c$ (where n is 0 or 1 if R$^b$ and R$^c$ are both independently alkyl, cycloalkyl or cycloalkylalkyl, and 0 if not) and —S(O)$_n$R$^d$ (where n is an integer from 0 to 2), with the understanding that the point of attachment of the heteroalkyl moiety is through a carbon atom, wherein R$^a$ is hydrogen, acyl, alkoxycarbonyl, alkyl, hydroxyalkyl, alkoxyalkyl, alkylsulfonyl, aminocarbonyl, aminosulfonylamino, cycloalkyl, or cycloalkylalkyl; R$^b$ and R$^c$ are independently of each other hydrogen, acyl, alkoxycarbonyl, aminocarbonyl, aminocarbonyl, aminosulfonylamino, hydroxyalkyl, alkoxyalkyl, alkylsulfonyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, R$^d$ is hydrogen, alkyl, cycloalkyl, cycloalkylalkyl, or aryl, and when n is 1 or 2, R$^d$ is alkyl, cycloalkyl, cycloalkylalkyl, hydroxyalkyl, alkoxyalkyl, alkylamino, aminocarbonyl, aminosulfonylamino, alkylsulfonyl, amino, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroalkoxy" means a group —OR wherein R is heteroalkyl as defined herein.

"Heteroalkylamino" means a group —NR'R wherein R' is hydrogen or alkyl and R is heteroalkyl as defined herein.

"Aminosulfonyl means a group —SO$_2$—NRR' wherein R and R' each independently is hydrogen or alkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroarylalkyl" refers to a moiety of the formula Ar$^z$—R$^y$—, where Ar$^z$ is heteroaryl and R$^y$ is alkylene as defined herein.

"Heterocyclyl" means a saturated or unsaturated non-aromatic cyclic moiety of 3 to 8 ring atoms in which one or two ring atoms are heteroatoms selected from N, O, or S(O)$_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —(X)$_n$—C(O)R$^e$ (where X is O or NR$^f$, n is 0 or 1, R$^e$ is hydrogen, alkyl, haloalkyl, hydroxy (when n is 0), alkoxy, amino, mono- and dialkylamino, or optionally substituted phenyl, and R$^f$ is H or alkyl), -alkylene-C(O)R$^g$ (where R$^g$ is alkyl, —OR$^h$ or NR$^i$R$^j$ and R$^h$ is hydrogen, alkyl or haloalkyl, and R$^i$ and R$^j$ are independently hydrogen or alkyl), and —S(O)$_n$R$^k$ (where n is an integer from 0 to 2) such that when n is 0, R$^k$ is hydrogen, alkyl, cycloalkyl, or cycloalkylalkyl, and when n is 1 or 2, R$^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —S(O)$_n$R$^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted", when used in association with "aryl", phenyl", "heteroaryl" "cycloalkyl" or "heterocyclyl", means an aryl, phenyl, heteroaryl, cycloalkylyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or (—CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl), or as provided herein elsewhere.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, the structure encompasses both enantiomers associated with the chiral center.

Compounds of the Invention

The invention provides compounds of formula:

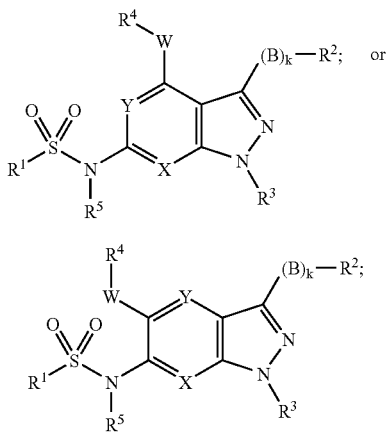

or a pharmaceutically acceptable salt thereof, wherein:

$R^1$ is aryl, heteroaryl, aralkyl or cycloalkyl;

$R^2$ is aryl, heteroaryl, cycloalkyl, branched alkyl or heterocyclyl;

$R^3$ is hydrogen or alkyl;

$R^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, —$(CHR^a)_r$—C(=O)—$R^b$, —$(CHR^a)_r$—O—C(=O)—$R^b$, —$(CHR^a)_r$—NH—C(=O)—$R^b$ or —$SO_2$—$R^b$, wherein $R^a$ is hydrogen, alkyl or heteroalkyl, $R^b$ is alkyl, hydroxy, amino, heteroalkyl, aryl, aralkyl, heteroaryl, or heterocyclyl, and r is from 0 to 4;

$R^5$ is hydrogen or alkyl;

W is a bond, O, $S(O)_m$, $CH_2$ or $NR^c$, wherein m is from 0 to 2, and $R^c$ is hydrogen, alkyl, heteroalkyl, heterocyclyl, hydroxycycloalkyl, —C(=O)—$R^d$ or —$SO_2$—$R^d$, wherein $R^d$ is alkyl, aryl, aralkyl, heteroaryl, heteroalkyl or heterocyclyl;

or $R^4$ and $R^c$ together with the atoms to which they are attached may form a heterocyclic ring;

X and Y each independently is nitrogen or $CR^e$, wherein $R^e$ is hydrogen, alkyl, hydroxy, alkoxy, amino, haloalkyl, cyano, halo, heteroalkyl, C(=O)—$R^f$ or —$SO_2$—$R^f$, wherein $R^f$ is hydrogen, hydroxy or alkyl;

k is 0 or 1; and

B is O, $S(O)_j$, $CH(OR^g)$, $NR^h$, C(=O), or $NR^iC$(=O), wherein j is 0, 1 or 2;

$R^g$ is hydrogen or alkyl, $R^h$ is hydrogen, alkyl, —C(=O)—$R^j$, or —$SO_2R^k$, wherein $R^j$ is alkyl, aryl or aralkyl; and $R^k$ is alkyl, and $R^i$ is alkyl, cycloalkyl, aryl or heteroaryl.

In many embodiments of the invention, the subject compounds are of formula Ia.

In certain embodiments of either formula Ia or Ib, k is 0.

In certain embodiments of the invention, X and Y are $CR^e$. Preferably $R^e$ is hydrogen.

In certain embodiments of either formula Ia or Ib, $R^3$ is hydrogen.

In certain embodiments of either formula Ia or Ib, $R^5$ is hydrogen.

In certain embodiments of either formula Ia or Ib, k is 0 and W is a bond.

In certain embodiments of either formula Ia or Ib, k is 0, W is a bond, and $R^4$ is hydrogen.

In certain embodiments of either formula Ia or Ib, k is 0, W is a bond, and $R^3$, $R^4$ and $R^5$ are hydrogen.

In certain embodiments of either formula Ia or Ib, k is 0, W is a bond, $R^3$, $R^4$ and $R^5$ are hydrogen, and X and Y are $CR^e$.

In certain embodiments of either formula Ia or Ib, k is 0, W is a bond, $R^3$, $R^4$ and $R^5$ are hydrogen, X and Y are $CR^e$, and $R^e$ is hydrogen.

In certain embodiments of either formula Ia or Ib, k is 0, W is a bond, $R^3$, $R^4$ and $R^5$ are hydrogen, X and Y are $CR^e$, $R^e$ is hydrogen, and $R^1$ and $R^2$ are optionally substituted phenyl.

In certain embodiments of either formula Ia or Ib, k is 0, W is a bond, $R^3$, $R^4$ and $R^5$ are hydrogen, X and Y are $CR^e$, $R^e$ is hydrogen, and $R^1$ and $R^2$ are aryl, preferably phenyl substituted once or twice with halo.

In certain embodiments of either formula Ia or Ib, k is 0, W is a bond, $R^3$, $R^4$ and $R^5$ are hydrogen, X and Y are $CR^e$, $R^e$ is hydrogen, and $R^1$ is phenyl optionally substituted one, two or three times with halo, haloalkyl, haloalkoxy, alkyl, alkoxy, cyano, alkylsulfonyl, alkoxycarbonyl, alkylcarbonylamino or alkylcarbonyl.

In certain embodiments of either formula Ia or Ib, k is 0, W is a bond, $R^3$, $R^4$ and $R^5$ are hydrogen, X and Y are $CR^e$, $R^e$ is hydrogen, $R^1$ is phenyl, 2-fluorophenyl, 3-fluorophenyl, 4-fluorophenyl, 2,4-difluorophenyl, 2,5-difluorophenyl, 3,5-difluorophenyl, 2,4,5-trifluorophenyl, 2-chlorophenyl, 3-chlorophenyl, 4-chlorophenyl, 2-chloro-4-fluorophenyl, 3-chloro-4-fluorophenyl, 2-methoxyphenyl, 3-methoxyphenyl, 4-methoxyphenyl, 4-methylcarbonylamino-phenyl, 2-methoxycarbonyl-phenyl, 3-chloro-2-methoxyphenyl, 2-chloro-6-methoxyphenyl, 2-cyanophenyl, 3-cyanophenyl, 4-cyanophenyl, 2,5-dimethoxyphenyl, 3,4-dimethoxyphenyl, 2,5-dimethylphenyl, 2,4-dimethylphenyl, 2,4,6-trimethylphenyl, 2-methylphenyl, 3-methylphenyl, 4-methylphenyl, 2-trifluoromethoxyphenyl, 4-trifluoromethoxyphenyl, 2-trifluoromethylphenyl, 3-trifluoromethylphenyl, 4-trifluoromethylphenyl, 2,4-di-(trifluoromethyl)-phenyl, 2-chloro-3-methylcarbonylamino-phenyl, 4-fluoro-2-methylphenyl, 3-chloro-4-methylphenyl, 5-chloro-2-methoxyphenyl, 2-methoxy-5-methylphenyl, 4-acetylphenyl, 3-methanesulfonyl-phenyl, 3-chloro-2-fluorophenyl, 3-fluoro-2-methylphenyl and 3-chloro-2-fluorophenyl, and $R^2$ is 2-chlorophenyl or 2-methoxyphenyl.

In certain embodiments of formula Ia, k is 1 and B is $NR^h$.

In certain embodiments of formula Ia, k is 1, B is $NR^h$, and $R^2$ is branched alkyl.

In certain embodiments of formula Ia, k is 1, B is $NR^h$, $R^2$ is branched alkyl, and X and Y are $CR^e$.

In certain embodiments of formula Ia, k is 1, B is $NR^h$, $R^2$ is branched alkyl, X and Y are $CR^e$, W is a bond, and $R^4$ and $R^e$ are hydrogen.

In certain embodiments of formula Ia, k is 1, B is $NR^h$, $R^2$ is isopropyl, X and Y are $CR^e$, W is a bond, and $R^4$ and $R^e$ are hydrogen.

In certain embodiments of formula Ia, k is 1, B is $NR^h$, $R^2$ is isopropyl, X and Y are $CR^e$, W is a bond, and $R^4$, $R^e$ and $R^h$ are hydrogen.

In many embodiments of formula Ia, the subject compounds are more specifically of the formula II:

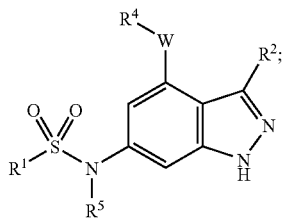

wherein W, $R^1$, $R^2$, $R^4$ and $R^5$ are as defined herein.

In certain embodiments of formula II, W is a bond.

In certain embodiments of formula II, W is a bond, and $R^4$ is hydrogen.

In certain embodiments of formula II, W is a bond, and $R^4$ and $R^5$ are hydrogen.

In certain embodiments of formula II, W is a bond, $R^3$, $R^4$ and $R^5$ are hydrogen, and X and Y are $CR^e$.

In certain embodiments of formula II, W is a bond, $R^4$ and $R^5$ are hydrogen, X and Y are $CR^e$, and $R^e$ is hydrogen.

In certain embodiments of formula II, W is a bond, $R^4$ and $R^5$ are hydrogen, X and Y are $CR^e$, $R^e$ is hydrogen, and $R^1$ and $R^2$ are optionally substituted phenyl.

In certain embodiments of formula II, W is a bond, $R^4$ and $R^5$ are hydrogen, X and Y are $CR^e$, $R^e$ is hydrogen, and $R^1$ and $R^2$ are phenyl substituted once or twice with halo.

In certain embodiments of formula II, W is a bond, $R^4$ and $R^5$ are hydrogen, X and Y are $CR^e$, $R^e$ is hydrogen, and $R^1$ is phenyl optionally substituted one, two or three times with halo, haloalkyl, haloalkoxy, alkyl, alkoxy, cyano, alkylsulfonyl, alkoxycarbonyl, alkylcarbonylamino or alkylcarbonyl.

In certain embodiments of formula II, W is a bond, $R^4$ and $R^5$ are hydrogen, X and Y are $CR^e$, $R^e$ is hydrogen, $R^1$ is phenyl, 2-fluorophenyl, 3-fluorophenyl, 4-fluorophenyl, 2,4-difluorophenyl, 2,5-difluorophenyl, 3,5-difluorophenyl, 2,4,5-trifluorophenyl, 2-chlorophenyl, 3-chlorophenyl, 4-chlorophenyl, 2-chloro-4-fluorophenyl, 3-chloro-4-fluorophenyl, 2-methoxyphenyl, 3-methoxyphenyl, 4-methoxyphenyl, 4-methylcarbonylamino-phenyl, 2-methoxycarbonyl-phenyl, 3-chloro-2-methoxyphenyl, 2-chloro-6-methoxyphenyl, 2-cyanophenyl, 3-cyanophenyl, 4-cyanophenyl, 2,5-dimethoxyphenyl, 3,4-dimethoxyphenyl, 2,5-dimethylphenyl, 2,4-dimethylphenyl, 2,4,6-trimethylphenyl, 2-methylphenyl, 3-methylphenyl, 4-methylphenyl, 2-trifluoromethoxyphenyl, 4-trifluoromethoxyphenyl, 2-trifluoromethylphenyl, 3-trifluoromethylphenyl, 4-trifluoromethylphenyl, 2,4-di-(trifluoromethyl)-phenyl, 2-chloro-3-methylcarbonylamino-phenyl, 4-fluoro-2-methylphenyl, 3-chloro-4-methylphenyl, 5-chloro-2-methoxyphenyl, 2-methoxy-5-methylphenyl, 4-acetylphenyl, 3-methanesulfonyl-phenyl, 3-chloro-2-fluorophenyl, 3-fluoro-2-methylphenyl and 3-chloro-2-fluorophenyl, and $R^2$ is 2-chlorophenyl or 2-methoxyphenyl.

In certain embodiments the compounds of the invention are of formula III:

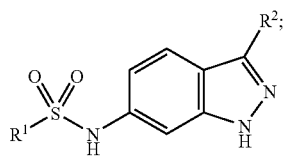

wherein $R^1$ and $R^2$ are as defined herein.

In certain embodiments of formula III, W is a bond.

In certain embodiments of formula III, $R^1$ is aryl.

In certain embodiments of formula III, $R^2$ is aryl.

In certain embodiments of formula III, $R^1$ and $R^2$ are optionally substituted phenyl.

In certain embodiments of formula III, $R^1$ and $R^2$ are phenyl substituted once or twice with halo.

In certain embodiments of formula III, $R^1$ and $R^2$ are phenyl substituted once or twice with fluoro or chloro.

In certain embodiments of formula III, $R^1$ is phenyl optionally substituted one, two or three times with halo, haloalkyl, haloalkoxy, alkyl, alkoxy, cyano, alkylsulfonyl, alkoxycarbonyl, alkylcarbonylamino or alkylcarbonyl.

In certain embodiments of formula III, $R^1$ is phenyl, 2-fluorophenyl, 3-fluorophenyl, 4-fluorophenyl, 2,4-difluorophenyl, 2,5-difluorophenyl, 3,5-difluorophenyl, 2,4,5-trifluorophenyl, 2-chlorophenyl, 3-chlorophenyl, 4-chlorophenyl, 2-chloro-4-fluorophenyl, 3-chloro-4-fluorophenyl, 2-methoxyphenyl, 3-methoxyphenyl, 4-methoxyphenyl, 4-methylcarbonylamino-phenyl, 2-methoxycarbonyl-phenyl, 3-chloro-2-methoxyphenyl, 2-chloro-6-methoxyphenyl, 2-cyanophenyl, 3-cyanophenyl, 4-cyanophenyl, 2,5-dimethoxyphenyl, 3,4-dimethoxyphenyl, 2,5-dimethylphenyl, 2,4-dimethylphenyl, 2,4,6-trimethylphenyl, 2-methylphenyl, 3-methylphenyl, 4-methylphenyl, 2-trifluoromethoxyphenyl, 4-trifluoromethoxyphenyl, 2-trifluoromethylphenyl, 3-trifluoromethylphenyl, 4-trifluoromethylphenyl, 2,4-di-(trifluoromethyl)-phenyl, 2-chloro-3-methylcarbonylamino-phenyl, 4-fluoro-2-methylphenyl, 3-chloro-4-methylphenyl, 5-chloro-2-methoxyphenyl, 2-methoxy-5-methylphenyl, 4-acetylphenyl, 3-methanesulfonyl-phenyl, 3-chloro-2-fluorophenyl, 3-fluoro-2-methylphenyl and 3-chloro-2-fluorophenyl, and $R^2$ is 2-chlorophenyl or 2-methoxyphenyl.

In certain embodiments the compounds of the invention are of formula IV:

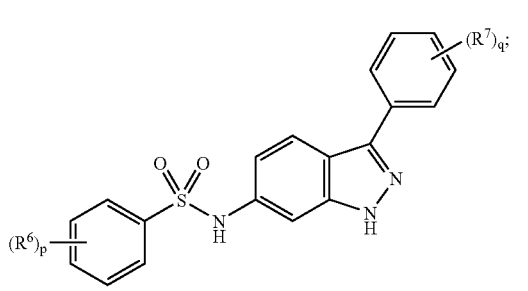

wherein:

p and q each independently is independently from 0 to 4;

each $R^6$ is independently halo, haloalkyl, haloalkoxy, alkyl, alkoxy, cyano, alkylsulfonyl, alkoxycarbonyl, alkylcarbonylamino or alkylcarbonyl; and each $R^7$ is independently halo, alkyl, alkoxy, haloalkyl, cyano, heteroalkyl, heterocyclyl, heteroalkoxy, heteroalkylamino, alkylsulfonyl, aminosulfonyl, hydroxycycloalkyl or —C(=O)—R″;

wherein

R″ is alkyl, heteroalkyl, aryl, aralkyl, heteroaryl or heterocyclyl.

In certain embodiments of formula IV, p is 1, 2 or 3 and each $R^6$ is independently fluoro, chloro, methoxy, methylcarbonylamino, methoxycarbonyl, cyano, methyl, trifluoromethyl, trifluoromethoxy, or acetyl.

In certain embodiments of formula IV, p is 1 or 2 and each $R^6$ is independently fluoro or chloro.

In certain embodiments of formula IV, q is 1 or 2 and $R^7$ is halo or alkoxy.

In certain embodiments of formula IV, q is 1 and $R^7$ is chloro or methoxy.

In embodiments of the invention where any of $R^1$, $R^2$, $R^3$, $R^4$, $R^5$, $R^6$, $R^7$, $R^a$, $R^b$, $R^c$, $R^d$, $R^e$, $R^f$, $R^g$, $R^h$, $R^i$, $R^j$, $R^k$, $R^m$ or R″ is alkyl or contains an alkyl moiety, such alkyl is preferably lower alkyl, i.e. $C_1$-$C_6$alkyl, and more preferably $C_1$-$C_4$alkyl.

In embodiments of the invention where $R^1$ or $R^2$ is heteroaryl, such heteroaryl is preferably thienyl, furanyl, pyridinyl or pyrimidinyl, each of which may be optionally substituted.

In embodiments of the invention where $R^1$ or $R^2$ is cycloalkyl, such cyclalkyl is preferably cyclopropyl, cyclobutyl, cyclopentyl or cyclohexyl, each of which may be optionally substituted.

In embodiments of the invention where $R^1$ is heterocyclyl, such heterocyclyl is preferably piperidinyl, pyrroldinyl, tetrahydropyranyl or tetrahydrofuranyl.

In embodiments of the invention where $R^2$ is aralkyl, such aralkyl is preferably benzyl or phenylethyl, which may be optionally substituted on the phenyl portions thereof.

In embodiments of the invention where $R^2$ is branched alkyl, such branched alkyl is preferably isopropyl, isobutyl or tert-butyl.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with the invention are shown below in Table 1.

TABLE 1

| # | Structure | Name (Autonom ™) | MP or M + H |
|---|---|---|---|
| 1 | 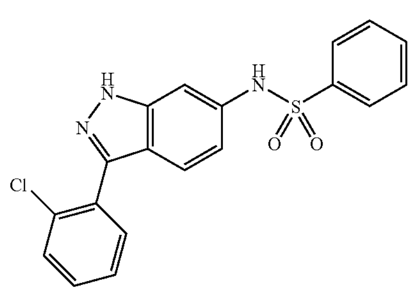 | N-[3-(2-Chloro-phenyl)-1H-indazol-6-yl]-benzenesulfonamide | 212.3-212.7° C. |

TABLE 1-continued

| # | Name (Autonom ™) | MP or M + H |
|---|---|---|
| 2 | N-[3-(2-Chloro-phenyl)-1H-indazol-6-yl]-2-fluoro-benzenesulfonamide | 251.1-252.3° C. |
| 3 | 2-Chloro-N-[3-(2-chloro-phenyl)-1H-indazol-6-yl]-benzenesulfonamide | 247.0-249.6° C. |
| 4 | N-[3-(2-Chloro-phenyl)-1H-indazol-6-yl]-4-fluoro-benzenesulfonamide | 197.1-198.2° C. |
| 5 | N-[3-(2-Chloro-phenyl)-1H-indazol-6-yl]-2,4-difluoro-benzenesulfonamide | 223.5-224.7° C. |
| 6 | N-[3-(2-Chloro-phenyl)-1H-indazol-6-yl]-4-methoxy-benzenesulfonamide | 269.7-270.2° C. |

TABLE 1-continued

| # | Structure | Name (Autonom ™) | MP or M + H |
|---|---|---|---|
| 7 | 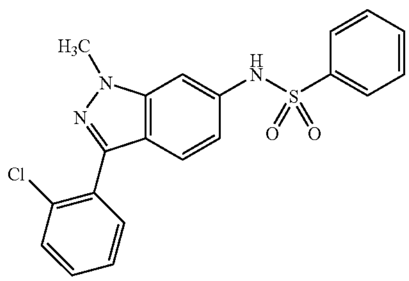 | N-[3-(2-Chloro-phenyl)-1-methyl-1H-indazol-6-yl]-benzenesulfonamide | 84.9-85.7° C. |
| 8 | 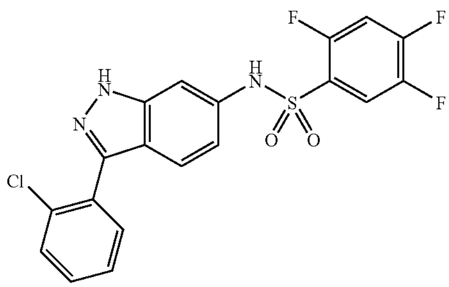 | N-[3-(2-Chloro-phenyl)-1H-indazol-6-yl]-2,4,5-trifluoro-benzenesulfonamide | 229.7-230.3° C. |
| 9 | 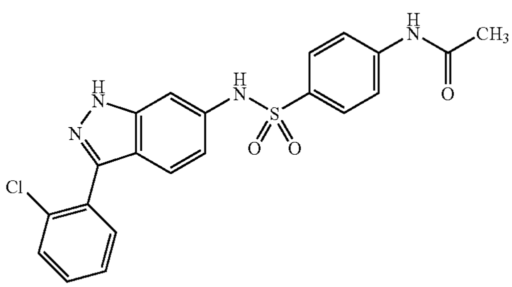 | N-{4-[3-(2-Chloro-phenyl)-1H-indazol-6-ylsulfamoyl]-phenyl}-acetamide | 443 |
| 10 | 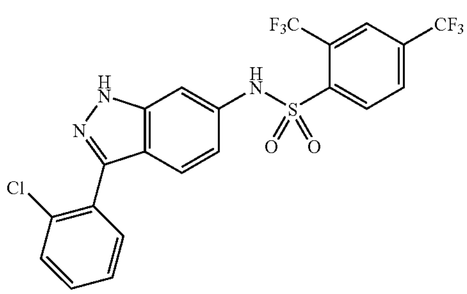 | N-[3-(2-Chloro-phenyl)-1H-indazol-6-yl]-2,4-bis-trifluoromethyl-benzenesulfonamide | 521 |
| 11 | 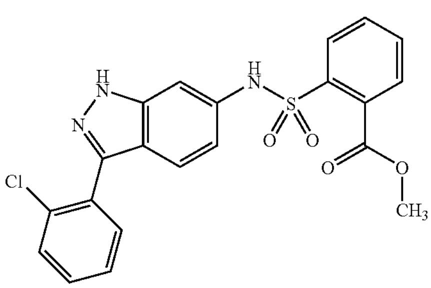 | 2-[3-(2-Chloro-phenyl)-1H-indazol-6-ylsulfamoyl]-benzoic acid methyl ester | 443 |

TABLE 1-continued

| # | Structure | Name (Autonom ™) | MP or M + H |
|---|---|---|---|
| 12 | 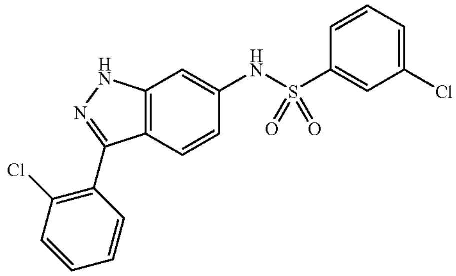 | 3-Chloro-N-[3-(2-chloro-phenyl)-1H-indazol-6-yl]-benzenesulfonamide | 187.4-189.0° C. |
| 13 | 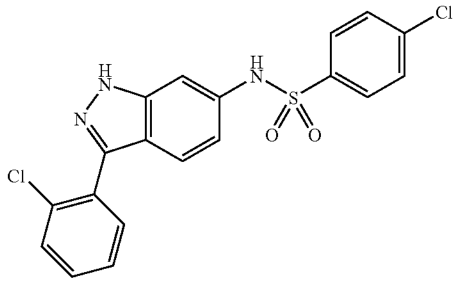 | 4-Chloro-N-[3-(2-chloro-phenyl)-1H-indazol-6-yl]-benzenesulfonamide | 419 |
| 14 | 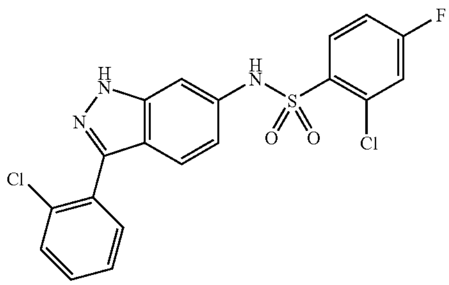 | 2-Chloro-N-[3-(2-chloro-phenyl)-1H-indazol-6-yl]-4-fluoro-benzenesulfonamide | 437 |
| 15 | 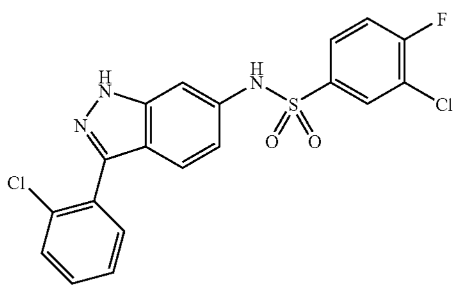 | 3-Chloro-N-[3-(2-chloro-phenyl)-1H-indazol-6-yl]-4-fluoro-benzenesulfonamide | 437 |
| 16 | 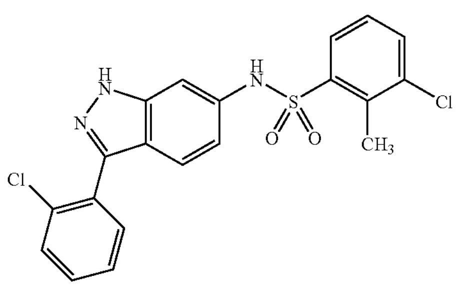 | 3-Chloro-N-[3-(2-chloro-phenyl)-1H-indazol-6-yl]-2-methyl-benzenesulfonamide | 433 |

TABLE 1-continued
| # | Structure | Name (Autonom ™) | MP or M + H |
|---|---|---|---|
| 17 | 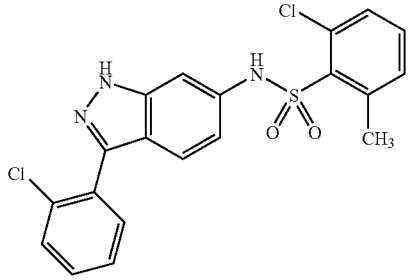 | 2-Chloro-N-[3-(2-chloro-phenyl)-1H-indazol-6-yl]-6-methyl-benzenesulfonamide | 433 |
| 18 | 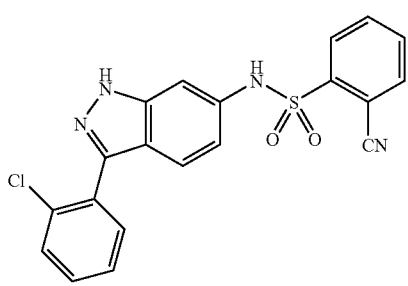 | N-[3-(2-Chloro-phenyl)-1H-indazol-6-yl]-2-cyano-benzenesulfonamide | 397 |
| 19 | 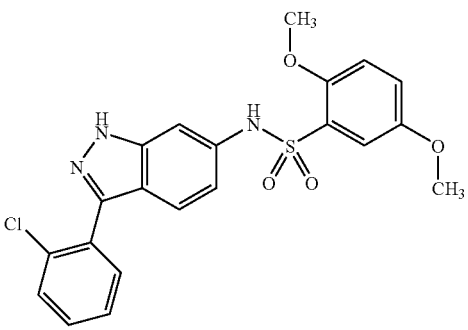 | N-[3-(2-Chloro-phenyl)-1H-indazol-6-yl]-2,5-dimethoxy-benzenesulfonamide | 445 |
| 20 | 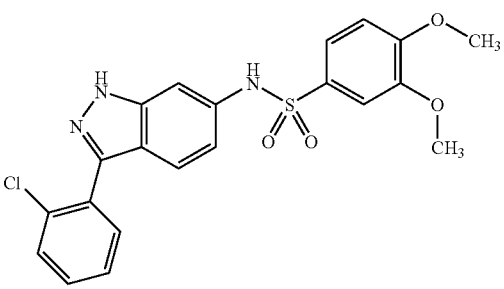 | N-[3-(2-Chloro-phenyl)-1H-indazol-6-yl]-3,4-dimethoxy-benzenesulfonamide | 445 |
| 21 | 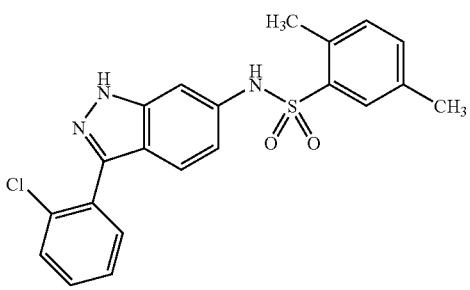 | N-[3-(2-Chloro-phenyl)-1H-indazol-6-yl]-2,5-dimethyl-benzenesulfonamide | 413 |

TABLE 1-continued

| # | Structure | Name (Autonom ™) | MP or M + H |
|---|---|---|---|
| 22 | 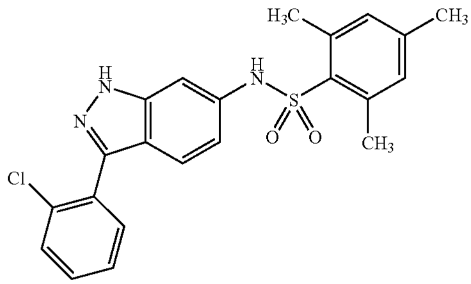 | N-[3-(2-Chloro-phenyl)-1H-indazol-6-yl]-2,4,6-trimethyl-benzenesulfonamide | 427 |
| 23 | 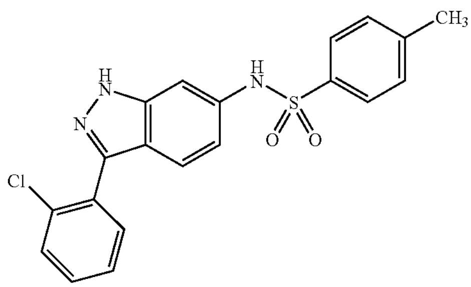 | N-[3-(2-Chloro-phenyl)-1H-indazol-6-yl]-4-methyl-benzenesulfonamide | 399 |
| 24 | 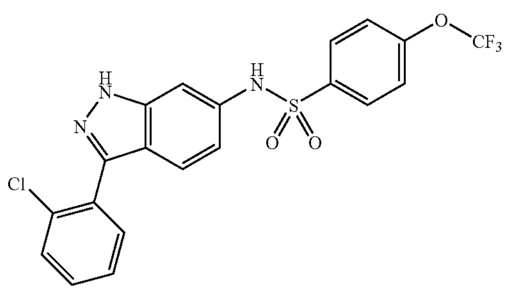 | N-[3-(2-Chloro-phenyl)-1H-indazol-6-yl]-4-trifluoromethoxy-benzenesulfonamide | 469 |
| 25 | 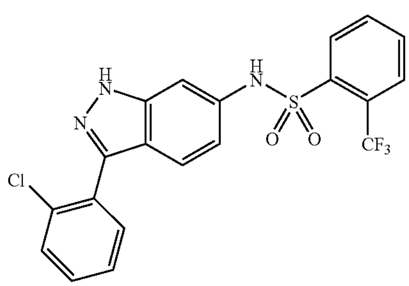 | N-[3-(2-Chloro-phenyl)-1H-indazol-6-yl]-2-trifluoromethyl-benzenesulfonamide | 453 |
| 26 | 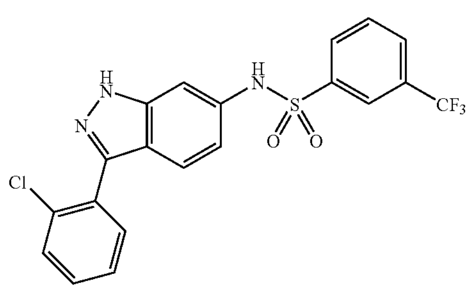 | N-[3-(2-Chloro-phenyl)-1H-indazol-6-yl]-3-trifluoromethyl-benzenesulfonamide | 453 |

TABLE 1-continued

| # | Structure | Name (Autonom ™) | MP or M + H |
|---|---|---|---|
| 27 | 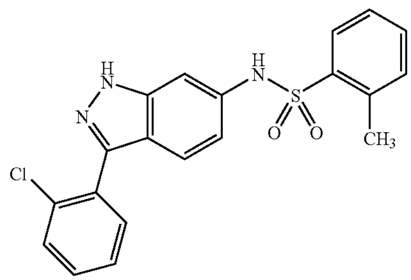 | N-[3-(2-Chloro-phenyl)-1H-indazol-6-yl]-2-methyl-benzenesulfonamide | 399 |
| 28 | 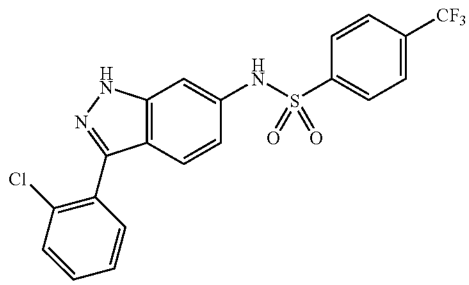 | N-[3-(2-Chloro-phenyl)-1H-indazol-6-yl]-4-trifluoromethyl-benzenesulfonamide | 453 |
| 29 | 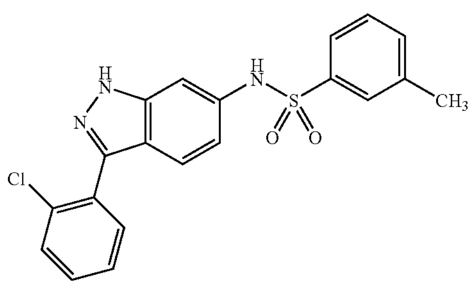 | N-[3-(2-Chloro-phenyl)-1H-indazol-6-yl]-3-methyl-benzenesulfonamide | 399 |
| 30 | 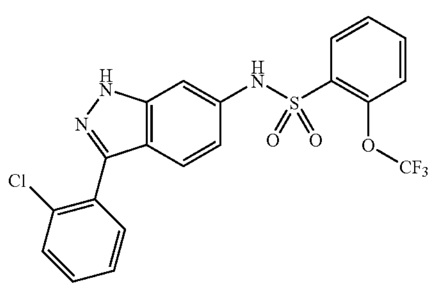 | N-[3-(2-Chloro-phenyl)-1H-indazol-6-yl]-2-trifluoromethoxy-benzenesulfonamide | 469 |
| 31 | 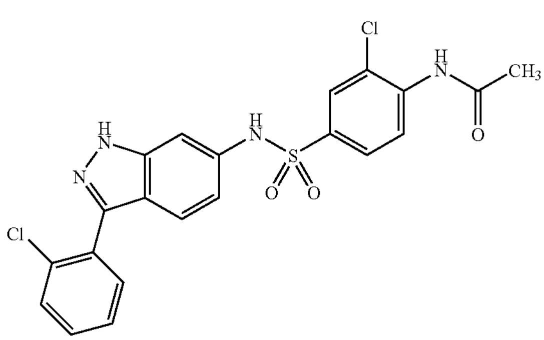 | N-{2-Chloro-4-[3-(2-chloro-phenyl)-1H-indazol-6-ylsulfamoyl]-phenyl}-acetamide | 476 |

TABLE 1-continued

| # | Structure | Name (Autonom ™) | MP or M + H |
|---|---|---|---|
| 32 | 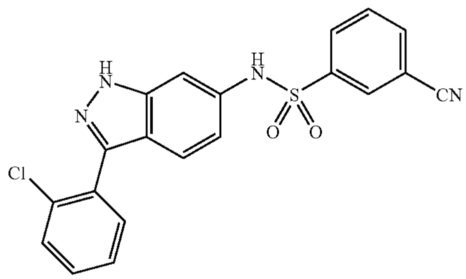 | N-[3-(2-Chloro-phenyl)-1H-indazol-6-yl]-3-cyano-benzenesulfonamide | 128.7-130.0° C. |
| 33 | 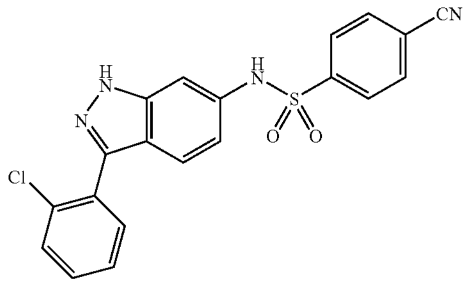 | N-[3-(2-Chloro-phenyl)-1H-indazol-6-yl]-4-cyano-benzenesulfonamide | 410 |
| 34 | 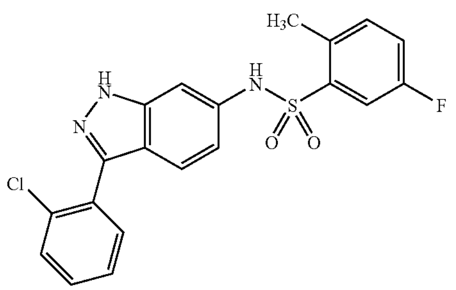 | N-[3-(2-Chloro-phenyl)-1H-indazol-6-yl]-5-fluoro-2-methyl-benzenesulfonamide | 236.6-236.9° C. |
| 35 | 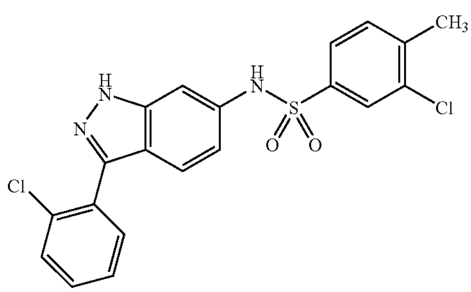 | 3-Chloro-N-[3-(2-chloro-phenyl)-1H-indazol-6-yl]-4-methyl-benzenesulfonamide | 433 |
| 36 | 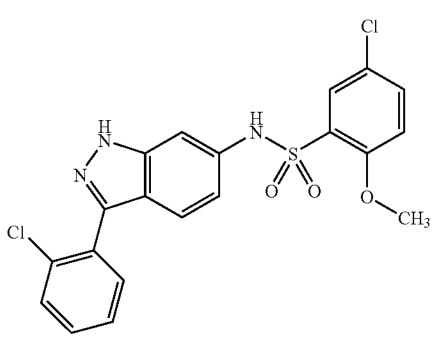 | 5-Chloro-N-[3-(2-chloro-phenyl)-1H-indazol-6-yl]-2-methoxy-benzenesulfonamide | 433 |

TABLE 1-continued

| # | Structure | Name (Autonom ™) | MP or M + H |
|---|---|---|---|
| 37 | 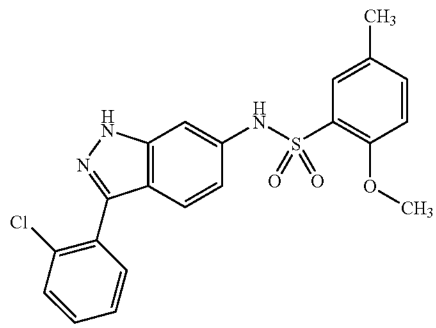 | N-[3-(2-Chloro-phenyl)-1H-indazol-6-yl]-2-methoxy-5-methyl-benzenesulfonamide | 429 |
| 38 | 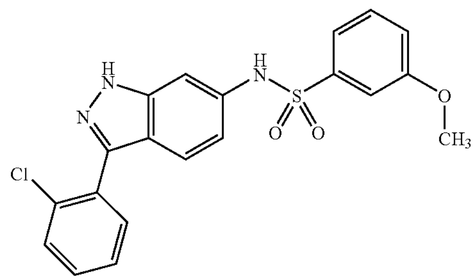 | N-[3-(2-Chloro-phenyl)-1H-indazol-6-yl]-3-methoxy-benzenesulfonamide | 415 |
| 39 | 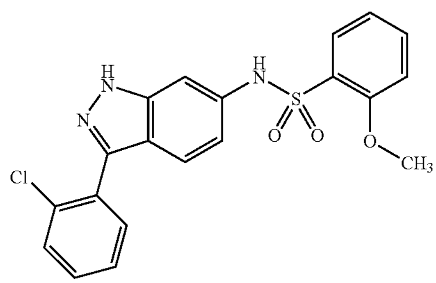 | N-[3-(2-Chloro-phenyl)-1H-indazol-6-yl]-2-methoxy-benzenesulfonamide | 415 |
| 40 | 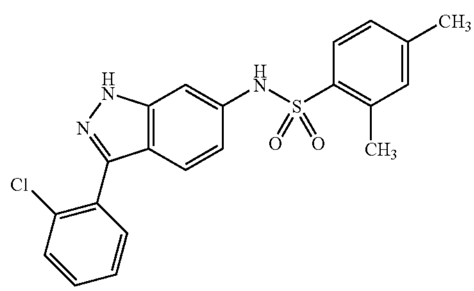 | N-[3-(2-Chloro-phenyl)-1H-indazol-6-yl]-2,4-dimethyl-benzenesulfonamide | 413 |
| 41 | 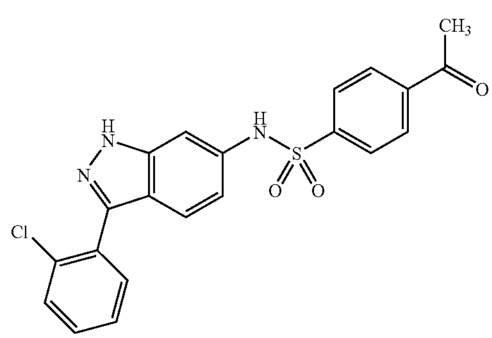 | 4-Acetyl-N-[3-(2-chloro-phenyl)-1H-indazol-6-yl]-benzenesulfonamide | 427 |

TABLE 1-continued

| # | Structure | Name (Autonom ™) | MP or M + H |
|---|---|---|---|
| 42 | 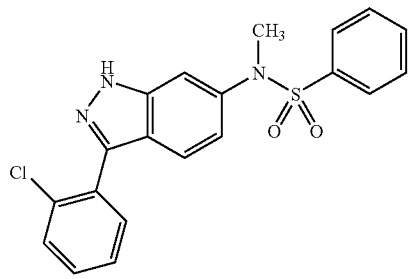 | N-[3-(2-Chloro-phenyl)-1H-indazol-6-yl]-N-methyl-benzenesulfonamide | 70.4-72.3° C. |
| 43 | 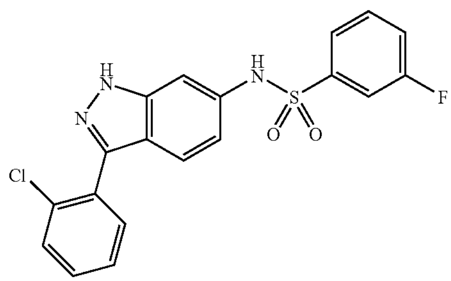 | N-[3-(2-Chloro-phenyl)-1H-indazol-6-yl]-3-fluoro-benzenesulfonamide | 198.8-199.7 |
| 44 | 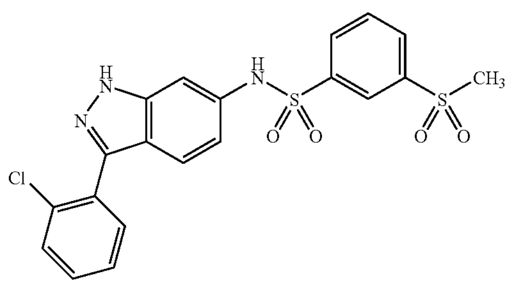 | N-[3-(2-Chloro-phenyl)-1H-indazol-6-yl]-3-methanesulfonyl-benzenesulfonamide | 242.5-244.0 |
| 45 | 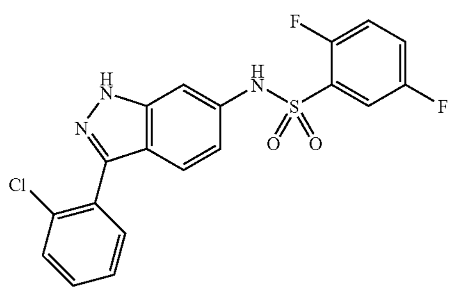 | N-[3-(2-Chloro-phenyl)-1H-indazol-6-yl]-2,5-difluoro-benzenesulfonamide | 230.0-231.4° C. |
| 46 | 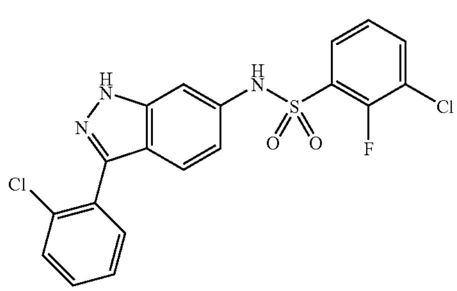 | 3-Chloro-N-[3-(2-chloro-phenyl)-1H-indazol-6-yl]-2-fluoro-benzenesulfonamide | 237.9-239.1° C. |

TABLE 1-continued

| # | Name (Autonom ™) | MP or M + H |
|---|---|---|
| 47 | N-[3-(2-Chloro-phenyl)-1H-indazol-6-yl]-3,5-difluoro-benzenesulfonamide | 232.7-234.1° C. |
| 48 | N-[3-(2-Chloro-phenyl)-1H-indazol-6-yl]-5-fluoro-2-methyl-benzenesulfonamide | 236.6-236.9° C. |
| 49 | 5-Chloro-N-[3-(2-chloro-phenyl)-1H-indazol-6-yl]-2-fluoro-benzenesulfonamide | 231.9-233.8° C. |
| 50 | 3-Chloro-N-[3-(2-methoxy-phenyl)-1H-indazol-6-yl]-benzenesulfonamide | 202.2-202.5° C. |
| 51 | N-(3-Isopropylamino-1H-indazol-6-yl)-benzenesulfonamide | 331 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing pyrazolopyrimidine compounds of the invention is shown in Scheme A below, wherein W, X, Y, p, q, $R^4$, $R^6$ and $R^7$ are as defined herein.

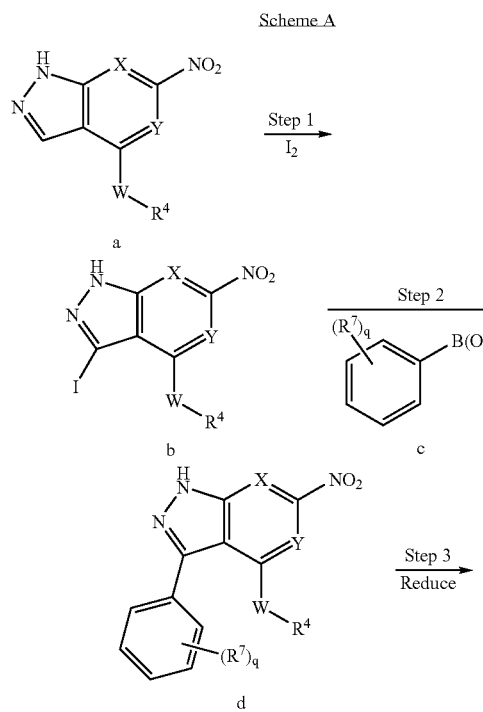

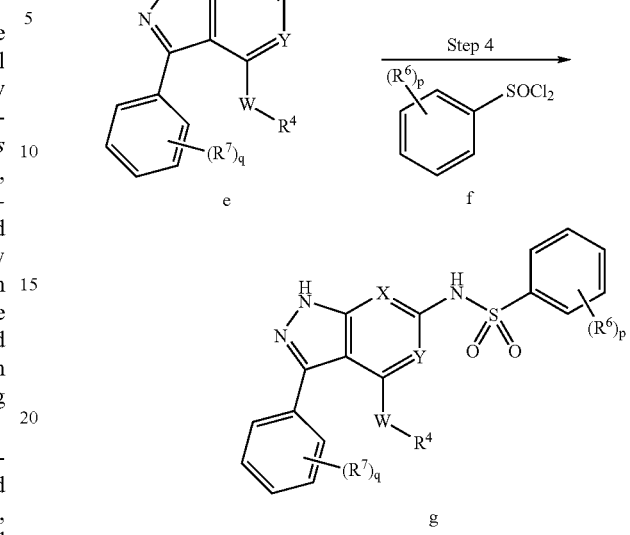

In step 1 of Scheme A, nitroindazole compound a is treated with iodine or iodine equivalent to form 3-iodo indazole compound b. The amine functionality at the 1-position may be protected (not shown) prior to carrying out this step, and then subsequently deprotected. In step 2 the iodoindazole b is reacted with aryl boronic acid c in the presence of suitable palladium catalyst to afford 3-aryl indazole d. Aryl boronic acid c may in certain embodiments be replaced with a corresponding heteroaryl boronic acid. In step 3 the nitro group on indazole compound d is reduced to yield amino-substituted indazole e. Indazole e in step 4 is then treated with arylsulfonyl chloride f to form the sulfonamide compound g, Compound g is a compound of formula Ia in accordance with the invention.

Another synthetic route to the compounds of the invention is shown in Scheme B, wherein W, X, Y, p, q, $R^4$, $R^6$ and $R^7$ are as defined herein.

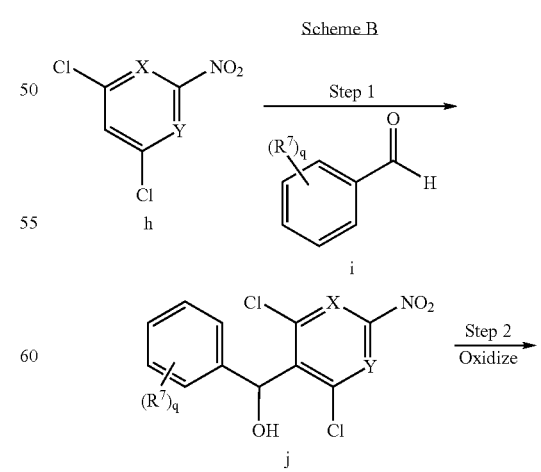

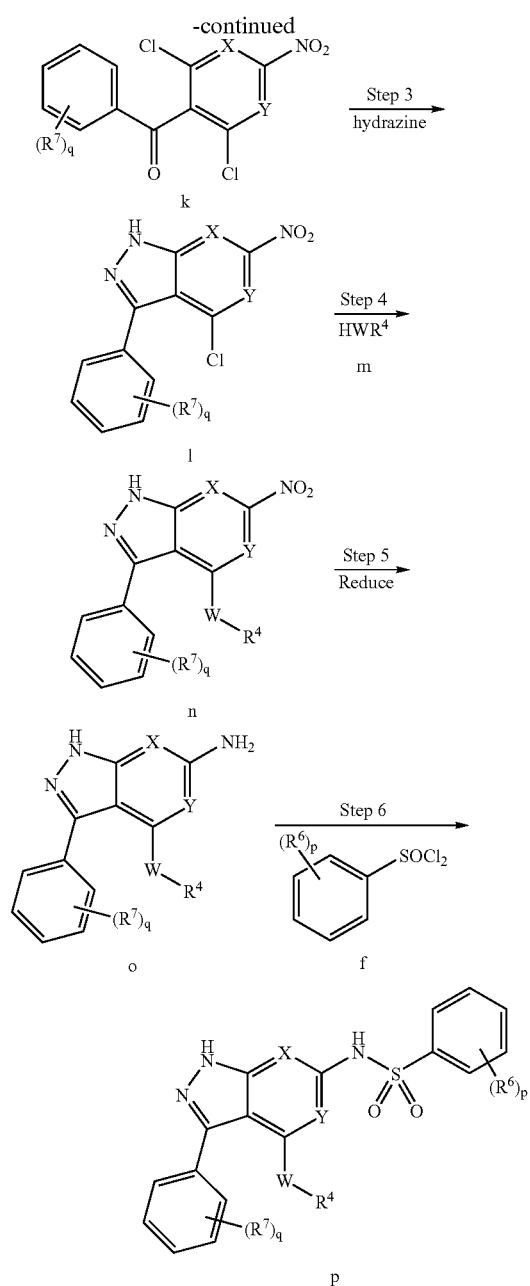

In step 1 of Scheme B. dichoronitro aryl compound h is deprotonated using a base, such as lithium diisopropylamide (LDA) or other suitable base, and then reacted with a benzaldehyde i or its derivative to produce an alcohol j. The alcohol compound j is oxidized in step 2, e.g., by manganese oxide, to produce phenyl ketone k. Reacting the ketone k with hydrazine in step 3 achieves a ring closure to provide indazole compound l. Reaction of compound l in step 4 with a nucleophile such as compound m (amine where W=N, alcohol where W=O, or thiol where W=S) displaces the chloro group on compound l to afford indazole compound n. In step 5, the nitro group of compound n is reduced to give the corresding amino compound o, which in turn is treated with aryl thionyl chloride f as described above for Scheme A, to afford indazole compound p. Compound p is a compound of formula Ia in accordance with the invention. Where the group —W—R⁴ is already present on dichloronitro compound h (or where W is a bond and H is hydrogen, step 4 may be omitted.

One of skill in the art will understand that certain modifications to the above schemes are contemplated and within the scope of the present invention. For example, certain steps will involve the use of protecting groups for functional groups that are not compatible with particular reaction conditions.

More specific details for producing compounds of formula (I) are described in the Examples section below.

Pharmaceutical Compositions and Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosus (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), cancer, multiple myeloma, and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

| ABBREVIATIONS | |
|---|---|
| DCM | dichloromethane |
| DMF | N,N-dimethylformamide |
| DMAP | 4-dimethylaminopyridine |
| EtOAc | ethyl acetate |
| EtOH | ethanol |
| gc | gas chromatography |
| HMPA | hexamethylphosphoramide |
| hplc | high performance liquid chromatography |
| mCPBA | m-chloroperbenzoic acid |
| MeCN | acetonitrile |
| NMP | N-methyl pyrrolidinone |
| TEA | triethylamine |
| THF | tetrahydrofuran |
| LDA | lithium diisopropylamine |
| TLC | thin layer chromatography |

Example 1

3-Chloro-N-[3-(2-chloro-phenyl)-1H-indazol-6-yl]-benzenesulfonamide

The synthetic procedure used in this Example is outlined in Scheme C below.

SCHEME C

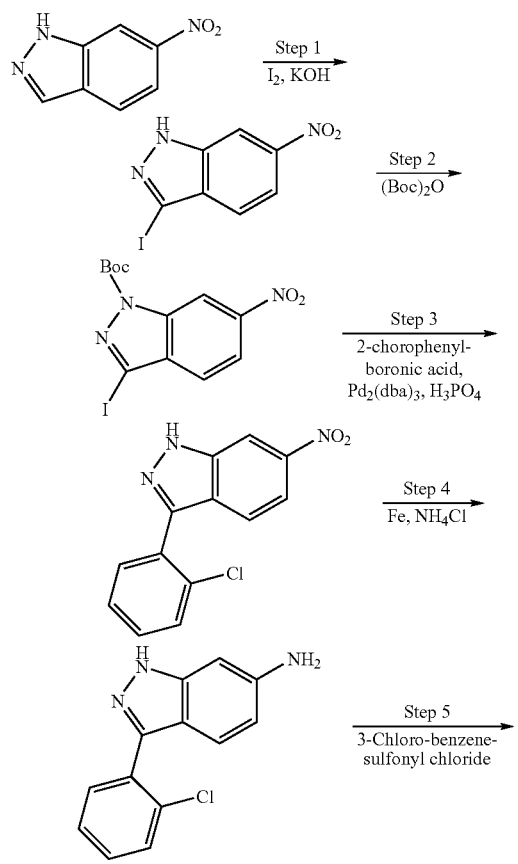

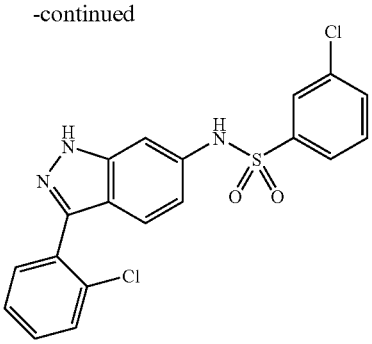

Step 1. 3-Iodo-6-nitro-1H-indazole

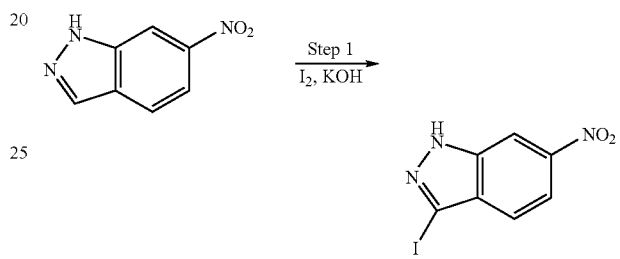

6-Nitro-indazol (4.0 g, 24.52 mmol), prepared using the procedure of *Tetrahedron* (1999), 6917-6922, was dissolved in 60 mL of DMF and iodine (12.4 g) and KOH (5.23 g) were added successively. The reaction mixture was stirred at room temperature for 1.5 hours, then poured into 10% aqueous $NaHSO_3$. The aqueous mixture was extracted three times with 150 mL EtOAc, and the combined organic layers were washed with water and brine, dried over $MgSO_4$, filtered, and concentrated under reduced pressure to give 7.01 g of crude 3-Iodo-6-nitro-1H-indazole.

Step 2. 3-Iodo-6-nitro-indazole-1-carboxylic acid tert-butyl ester

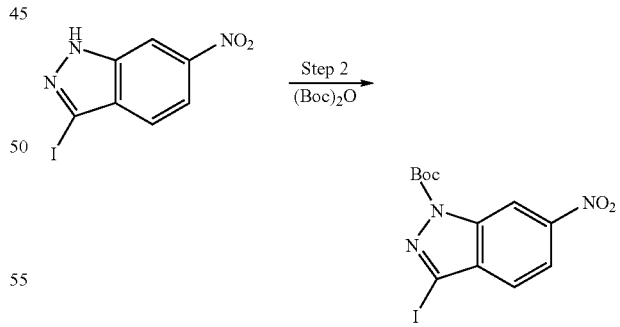

3-Iodo-6-nitro-1H-indazole (7.01 g, 24.25 mmol), 4-(dimethylamino)pyridine (4.44 g) and 6.34 mL of N,N-diisopropyl ethylamine were dissolved in 500 mL of $CH_2Cl_2$ and the mixture was cooled to 0° C. $(BOC)_2O$ (7.94 g) was added to the stirring mixture, and the mixture was allowed to warm to room temperature with stirring for 2 hours at room temperature. The reaction was quenched by addition of 400 mL $H_2O$, and the organic layer was separated, washed with brine, dried over $MgSO_4$, filtered and evaporated under reduced perssure.

The residue was chromatographed with silica gel (hexanes/EtOAc 0-80%) to give 7.81 g of 3-Iodo-6-nitro-indazole-1-carboxylic acid tert-butyl ester.

Step 3 3-(2-Chloro-phenyl)-6-nitro-1H-indazole

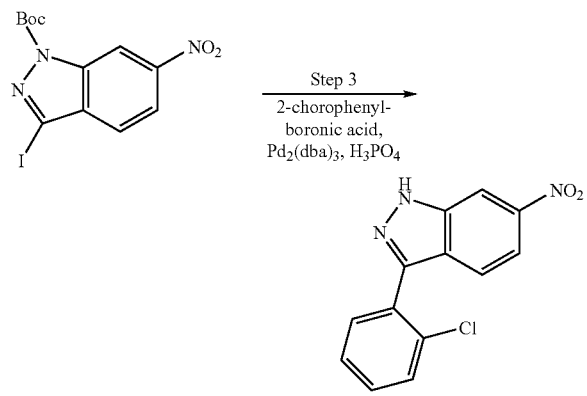

To a solution of 3-Iodo-6-nitro-indazole-1-carboxylic acid tert-butyl ester (5.83 g, 14.98 mmol) in 200 mL toluene was added 2-chlorophenyl boronic acid (4.48 g, 28.46 mmol), $K_3PO_4$ (7.82 g), $Pd_2(dba)_3$ (41.53 mg) and 2-(dicyclohexylphosphino)-2'-methylbiphenyl) (436.68 mg). The reaction mixture was heated to 110° C. and stirred at this temperature for 36 hours. The reaction mixture was cooled and partitioned between water and EtOAc. The orgaic layer was separated, dried over $MgSO_4$, filtered and concentrated under reduced pressure to give 8.82 g of crude 3-(2-Chloro-phenyl)-6-nitro-1H-indazole, MS (M+H)=275.

Step 4. 3-(2-Chloro-phenyl)-1H-indazol-6-ylamine

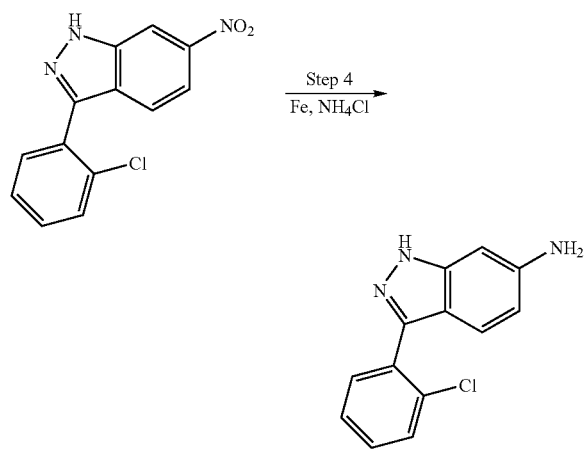

3-(2-Chloro-phenyl)-6-nitro-1H-indazole (8.82 g, 32.23 mmol) was dissolved in 400 mL EtOH and 120 mL water, and the mixture was heated to 85° C. with stirring. After stirring for 40 minutes, Fe (9.0 g, 161.15 mmol) and $NH_4Cl$ (8.62 g, 161.15 mmol) were added, and the reaction mixture was stirred for 16 hours at 85° C. The reactuion mixture was filtered through Whatman filter paper, and the filtrate was concentrated under reduced pressure. The resulting residue was partitioned between water and ethyl acetate, and the organic layer was separated, dried over $MgSO_4$, filtered and concentrated under reduced pressure. The residue was chromatographed through silica gel (hexanes/EtOAc 0-50%) to give 2.24 g of 3-(2-Chloro-phenyl)-1H-indazol-6-ylamine, MS (M+H)=245.

Step 5. 3-Chloro-N-[3-(2-chloro-phenyl)-1H-indazol-6-yl]-benzenesulfonamide

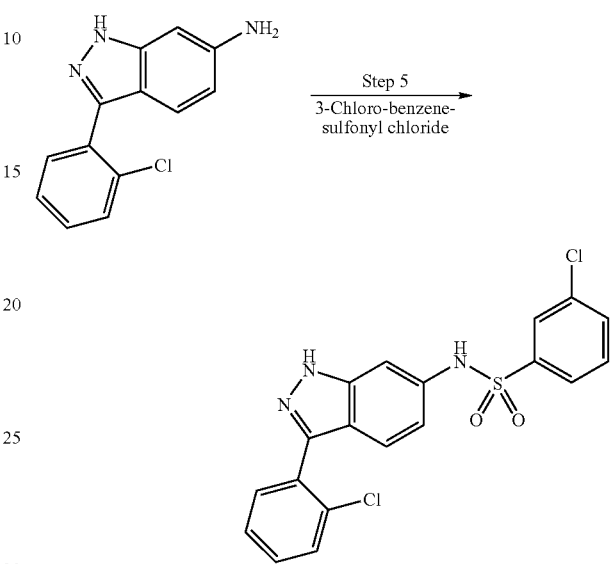

To 3-chlorobenzenesulfonyl chloride (43.4 mg, 0.205 mmol) in 1.0 mL pyridine was added 3-(2-chloro-phenyl)-1H-indazol-6-ylamine (50.0 mg, 0.205 mmol). The solution was heated to 120° C. and stirred for one hour, then cooled and concentrated under reduced pressure. The residue was chromatographed through silica gel (hexanes/EtOAc 0-30%) to give 51.0 mg of 3-Chloro-N-[3-(2-chloro-phenyl)-1H-indazol-6-yl]-benzenesulfonamide, MP=187-189° C., MS (M+H)=419.

Using the procedure of Example 1, but replacing the 3-chlorobenzenesulfonyl chloride in step 5 with other substituted benzenesulfonyl chlorides, and/or replacing the 2-chlorophenyl boronic acid of step 3 with other substituted phenyl boronic acids, produced several additional compounds which are shown in Table 1.

Example 2

N-(3-Isopropylamino-1H-indazol-6-yl)-benzenesulfonamide

The synthetic procedure used in this Example is outlined in Scheme D below.

SCHEME D

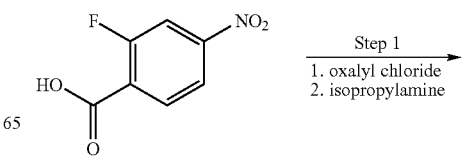

47

-continued

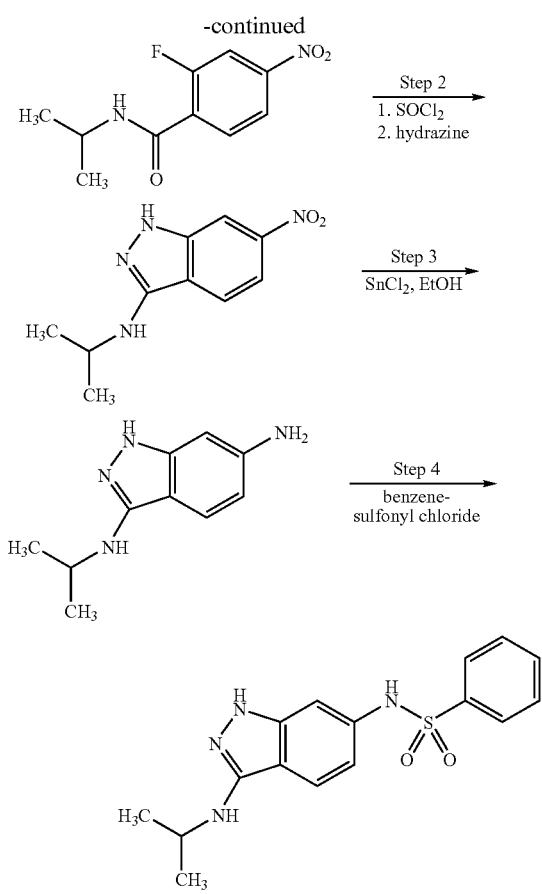

Step 1. 2-Fluoro-N-isopropyl-4-nitro-benzamide

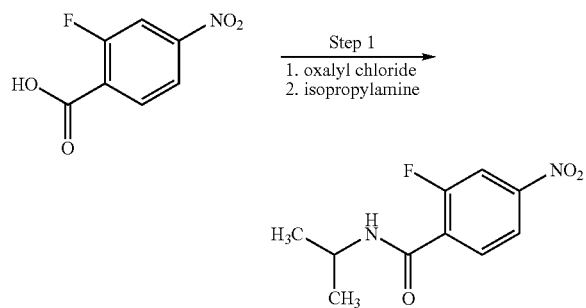

2-Fluoro-4-nitrobenzoic acid (1.002 g, 5.41 mmol) was dissolved in dichloromethane and cooled in an ice bath. DMF (0.1 mL) and oxalyl chloride (0.71 mL, 8.4 mmol) were added, and the reaction mixture was stirred at ice bath temperature (0-5° C.) for two houres. Dichloromethane (25 mL) was added, followed by isopropylamine (1.85 mL, 21.7 mmol). The ice bath was removed and the reaction mixture was stirred for 2.5 hours. The reaction mixture was washed with 25 mL of 10% aqueous NaOH solution, and the organic layer was separated, dried over MgSO₄, filtered and concentrated under reduced pressure. The residue was chromatographed through silica gel (EtOAc/hexanes 0-33%) to give 1,015 g of 2-fluoro-N-isopropyl-4-nitro-benzamide.

48

Step 2. Isopropyl-(6-nitro-1H-indazol-3-yl)-amine

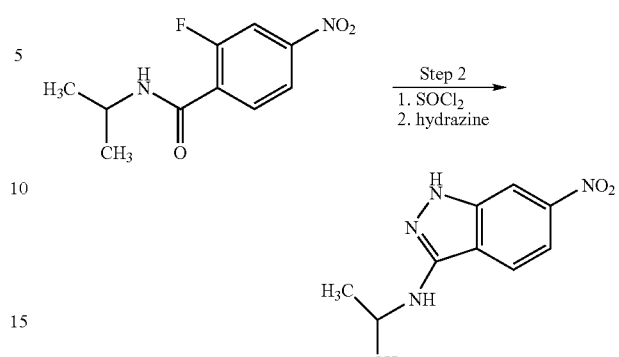

2-Fluoro-N-isopropyl-4-nitro-benzamide (0.204 g, 0.902 mmol) and thionyl chloride (1 mL) were heated to 78° C. and stirred for three hours. The reaction mixture was cooled and concentrated to a white solid. NMP (1 mL), hydrazine (0.28 mL, 8.92 mmol) and powdered K₂CO₃ were added, and the reation mixture was heated to 90° C. and stirred for two hours. The reaction mixture was cooled and partitioned between water and ethyl acetate. The organic layer was separated, dried over MgSO₄, filtered and concentrated under reduced pressure. The residue was chromatographed through silica gel (EtOAc/hexanes 0-33%) to give 0.075 g of Isopropyl-(6-nitro-1H-indazol-3-yl)-amine, MS (M+H)=249.

Step 3 N*3*-Isopropyl-1H-indazole-3,6-diamine

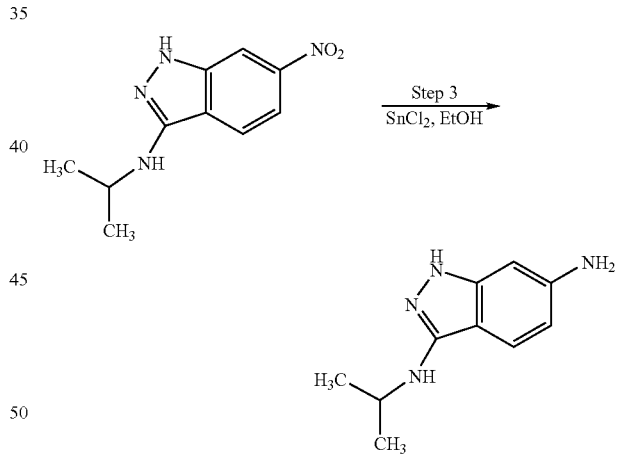

Isopropyl-(6-nitro-1H-indazol-3-yl)-amine (0.070 g, 0.318 mmol) and SnCL₂.2H₂O (0.365 g, 1.62 mmol) were added to 5 mL EtOH, and the reaction mixture was heated to 78° C. and stirred for four hours. The reaction mixture was cooled and concentrated under reduced pressure. The resulting oil was dissolved in 5 mL EtOH and the solution was treated with 5 mL saturated aqueous NaHCO₃. The resulting solid was removed by filtration, and the filtrate was washed with saturated aqueous NaHCO₃, dried over MgSO₄, filtered and concentrated under reduced pressure. The residue was chromatographed through silica gel (EtOAc/hexanes 0-100%) to give 0.036 g of N*3*-Isopropyl-1H-indazole-3, 6-diamine, MS (M+H)=219.

Step 4. N-(3-Isopropylamino-1H-indazol-6-yl)-benzenesulfonamide

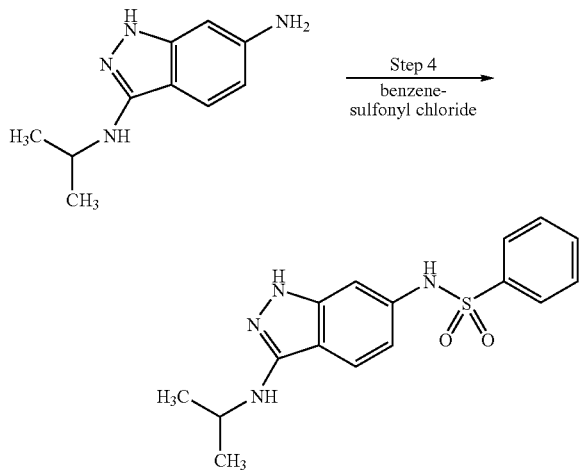

N*3*-Isopropyl-1H-indazole-3,6-diamine (0.036 g, 0.19 mmol) was dissolved in 1 mL pyridine and benzenesulfonyl chloride (0.024 mL, 0.19 mmol) was added. The reaction mixture was heated to 100° C. and stirred for an hour, then cooled and concentrated under reduced pressure. The residue was chromatographed through silica gel (EtOAc/hexanes 0-50%) to give 6.0 mg of N-(3-Isopropylamino-1H-indazol-6-yl)-benzenesulfonamide, MS (M+H)=359.

Example 3

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Using the above procedure, the compounds of the invention were found to be inhibitors of p38 MAP kinase. For example, 3-Chloro-N-[3-(2-chloro-phenyl)-1H-indazol-6-yl]-2-fluoro-benzenesulfonamide exhibited a p38 $IC_{50}$ (uM) of approximately 0.02.

Example 4

In Vitro Assay to Evaluate the Inhibition of LPS-induced TNF-α Production in THP1 Cells This example illustrates an in vitro assay to evaluate the inhibition of LPS-induced TNF-α production in THP1 cells.

The ability of the compounds of this invention to inhibit the TNF-α release is determined using a minor modification of the methods described in Blifeld, et al. *Transplantation*, 51:498-503 (1991).

(a) Induction of TNF Biosynthesis:

THP-1 cells are suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/mL and then plated in 96 well plate (0.2 mL aliquots in each well). Test compounds are dissolved in DMSO and then diluted with the culture medium such that the final DMSO concentration is 5%. Twenty five μL aliquots of test solution or only medium with DMSO (control) are added to each well. The cells are incubated for 30 min., at 37° C. LPS (Sigma, St. Louis, Mo.) is added to the wells at a final concentration of 0.5 μg/ml, and cells were incubated for an additional 2 h. At the end of the incubation period, culture supernatants are collected and the amount of TNF-α present is determined using an ELISA assay as described below.

(b) ELISA Assay:

The amount of human TNF-α present is determined by a specific trapping ELISA assay using two anti-TNF-α antibodies (2TNF-H12 and 2TNF-H34) described in Reimund, J. M., et al. *GUT*. Vol. 39(5), 684-689 (1996).

Polystyrene 96-well plates are coated with 50 μl per well of antibody 2TNF-H12 in PBS (10 μg/mL) and incubated in a humidified chamber at 4° C. overnight. The plates are washed with PBS and then blocked with 5% nonfat-dry milk in PBS for 1 hour at room temperature and washed with 0.1% BSA (bovine serum albumin) in PBS.

TNF standards are prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) are mixed with 25 μL aliquots of biotinylated monoclonal antibody 2TNF-H34 (2 μg/mL in PBS containing 0.1% BSA) and then added to each well. The samples are incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples are incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) is added to each well and the samples are incubated in the dark for 30 min., at room temperature. Optical density of the sample and the reference are read at 450 nm and 650 nm, respectively. TNF-α levels are determined from a graph relating the optical density at 450 nm to the concentration used.

Example 5

In Vitro Assay to Evaluate the Inhibition of LPS-induced TNF-α Production in THP1 Cells This example illustrates an in vivo assay to evaluate the inhibition of LPS-induced TNF-α production in mice (or rats).

The ability of the compounds of this invention to inhibit the TNF-α release, in vivo, is determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18-21 grams (Charles River, Hollister, Calif.) are acclimated for one week. Groups containing 8 mice each are dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice are injected intraperitoneally with 20 μg of LPS (Sigma, St. Louis, Mo.). After 1.5 h, the mice are sacrificed by $CO_2$ inhalation and blood is harvested by cardiocentesis. Blood is clarified by centrifugation at 15,600×g for 5 min., and sera are transferred to clean tubes and frozen at −20° C. until analyzed for TNF-α by ELISA assay (Biosource International, Camarillo, Calif.) following the manufacturer's protocol.

Example 6

Adjuvant-Induced Arthritis in Rats

AIA-induced arthritis is evaluluted using the procedure of Badger et al., *Arthritis & Rheumatism*, 43(1) pp 175-183 (2000) AIA is induced by a single injection of 0.75 mg of parrafin-suspended *Mycobacterium Butycricum*) into male Lewis rats. Hindpaw volume is measued by water displacement on days 15, 20 and 30. A set of control animals is dosed with tragacanth. Test compounds in 0.5% tragacanth are administered orally at 3, 10, 30 and 60 mg/kg/day dosages. Indomethacin is used as a positive control. Percentage inhibition of hindpaw edema is calculated by 1-[AIA(treated)/AIA (control)]×100 where AIA (treated) and AIA (control) represent the mean paw volume.

Example 7

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |

| Topical Formulation | |
| --- | --- |
| Ingredients | grams |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula (Ia)

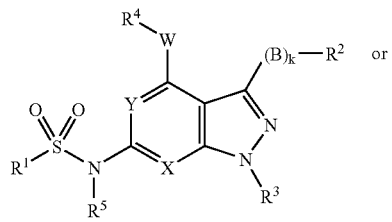

a pharmaceutically acceptable salt thereof, wherein $R^1$ is aryl, $R^2$ is 2-chlorophenyl or 2-methoxyphenyl;

$R^3$ is hydrogen;

$R^4$ is hydrogen $R^5$ is hydrogen or alkyl;

B is O; k is 0;

W is a bond; and X and Y each is —$CR^e$, wherein $R^e$ is hydrogen or alkyl.

2. The compound of claim 1, wherein $R^1$ is optionally substituted phenyl.

3. The compound of claim 2, wherein $R^e$ is hydrogen.

4. The compound of claim 3, wherein $R^1$ is phenyl optionally substituted one, two or three times with halo, haloalkyl, haloalkoxy, alkyl, alkoxy, cyano, alkylsulfonyl, alkoxycarbonyl, alkylcarbonylamino or alkylcarbonyl.

5. The compound of claim 4, wherein $R^1$ is phenyl, 2-fluorophenyl, 3-fluorophenyl, 4-fluorophenyl, 2,4-difluoropbenyl, 2,5-difluorophenyl, 3,5-difluorophenyl, 2,4,5-trifluorophenyl, 2-chlorophenyl, 3-chlorophenyl, 4-chlorophenyl, 2-chloro-4-fluorophenyl, 3-chloro-4-fluorophenyl, 2-methoxyphenyl, 3-methoxyphenyl, 4-methoxyphenyl, 4-methylcarbonylamino-phenyl, 2-methoxycarbonyl-phenyl, 3-chloro-2-methoxyphenyl, 2-chloro-6-metboxyphenyl, 2-cyanophenyl, 3-cyanophenyl, 4-cyanophenyl, 2,5-dimethoxyphenyl, 3,4-dimethoxyphenyl, 2,5-dimethy1pheny, 2,4-dimethylphenyl, 2,4,6-trimethylphenyl, 2-methylphenyl, 3-metbylphenyl, 4-methylphenyl, 2-trifluoromethoxyphenyl,4-trifluoromethoxyphenyl, 2-trifluoromethylphenyl, 3-trifluorormthylphenyl, 4-trifluoromethylphenyl, 2,4-di-(trifluorometyl)-phenyl, 2-chloro-3-methylcarbonylamino-phenyl, 4-fluora-2-methylphenyl, 3-chloro-4-methylphenyl, 5-chloro-2-methoxyphenyl, 2-metboxy-5-methylphenyl, 4-acetylphenyl, 3-methanesulfonyl-phenyl, 3-chloro-2-fluorophenyl, 3-fluoro-2-methylphenyl and 3-chloro-2-fluorophenyl.

6. A composition comprising:

(a) a pharmaccutically acceptable excipient; and (b) a compound of claim 1.

* * * * *